United States Patent
Bub et al.

(10) Patent No.: US 8,703,450 B2
(45) Date of Patent: Apr. 22, 2014

(54) WATER-ABSORBENT POLYMER STRUCTURES BASED ON RENEWABLE RESOURCES AND METHOD FOR PRODUCING SAID STRUCTURES

(75) Inventors: Günther Bub, Marl (DE); Jürgen Mosler, Castrop-Rauxel (DE); Andreas Sabbagh, Dulmen (DE); Franz-Felix Kuppinger, Marl (DE); Franck Furno, Düsseldorf (DE)

(73) Assignee: Evonik Degussa GmbH, Essen (DE)

( * ) Notice: Subject to any disclaimer, the term of this patent is extended or adjusted under 35 U.S.C. 154(b) by 1002 days.

(21) Appl. No.: 11/817,204

(22) PCT Filed: Feb. 28, 2006

(86) PCT No.: PCT/EP2006/001830
§ 371 (c)(1),
(2), (4) Date: Aug. 18, 2008

(87) PCT Pub. No.: WO2006/092271
PCT Pub. Date: Sep. 8, 2006

(65) Prior Publication Data
US 2009/0023006 A1    Jan. 22, 2009

(30) Foreign Application Priority Data
Feb. 28, 2005    (DE) .......................... 10 2005 009 584

(51) Int. Cl.
| | | |
|---|---|---|
| C08F 20/06 | (2006.01) | |
| C12P 7/02 | (2006.01) | |
| C12P 7/40 | (2006.01) | |
| C12P 7/42 | (2006.01) | |

(52) U.S. Cl.
USPC ............. 435/136; 435/132; 435/146; 526/75; 526/77; 526/317.1; 528/271; 528/425; 562/515; 562/599

(58) Field of Classification Search
CPC ............... C08F 20/06; C12P 7/02; C12P 7/40
USPC ........... 435/132, 136, 146; 526/317.1, 75, 77; 528/271, 425; 562/515, 599
See application file for complete search history.

(56) References Cited

U.S. PATENT DOCUMENTS 2,042,224 A    5/1936   Groll
2,352,641 A *  7/1944   Kung ........................... 562/588
(Continued)

FOREIGN PATENT DOCUMENTS

DE    4128692 A1    3/1993
DE    4238493 C1    4/1994
(Continued)

OTHER PUBLICATIONS

Wypych; Handbook of Fillers—A Definitive User's Guide and Databook (2nd Edition); 2000.*

(Continued)

*Primary Examiner* — Richard A Huhn
(74) *Attorney, Agent, or Firm* — Smith Moore Leatherwood LLP; Philip P. McCann; John P. Zimmer

(57) ABSTRACT

The present invention relates to a process for the production of polymers, such as water-absorbing polymer structures, by radical polymerization of acrylic acid, whereby the acrylic acid has been obtained by a synthesis process which comprises as a process step the splitting of an organic material by means of an enzyme or at least one component of an enzyme. The invention also relates to the water-absorbing polymers obtainable by this process, water-absorbing polymers which are based to at least about 25 wt % upon partially neutralized acrylic acid, a composite, a process for the production of a composite, the composite obtainable by this production, the use of acrylic acid in the production of polymers, preferably in the production of water-absorbing polymer structures, a device for the production of acrylic acid, and a process for the production of acrylic acid.

10 Claims, 2 Drawing Sheets

(56) References Cited

U.S. PATENT DOCUMENTS

| | | | |
|---|---|---|---|
| 2,469,701 A * | 5/1949 | Redmon | 562/599 |
| 2,558,520 A | 6/1951 | Hoyt | |
| 3,433,831 A * | 3/1969 | Aoshima et al. | 562/600 |
| 4,962,027 A * | 10/1990 | Slininger et al. | 435/147 |
| 5,387,720 A | 2/1995 | Neher et al. | |
| 5,463,121 A | 10/1995 | Sridhar | |
| 6,060,557 A | 5/2000 | Dahmen et al. | |
| 6,179,966 B1 | 1/2001 | Shimizu et al. | |
| 6,380,427 B1 * | 4/2002 | Miyazaki et al. | 562/600 |
| 6,403,700 B1 | 6/2002 | Dahmen et al. | |
| 6,414,190 B1 | 7/2002 | Eck et al. | |
| 6,444,744 B1 * | 9/2002 | Fujimaru et al. | 524/556 |
| 6,498,272 B1 | 12/2002 | Schröder et al. | |
| 6,679,939 B1 | 1/2004 | Thiel et al. | |
| 6,852,517 B1 * | 2/2005 | Suthers et al. | 435/135 |
| 6,939,991 B2 | 9/2005 | Thiel et al. | |
| 7,179,875 B2 | 2/2007 | Fuchs et al. | |
| 7,294,741 B2 | 11/2007 | Bub et al. | |
| 7,557,245 B2 | 7/2009 | Nordhoff et al. | |
| 7,557,246 B2 | 7/2009 | Nordhoff et al. | |
| 7,803,969 B2 | 9/2010 | Nordhoff et al. | |
| 7,939,597 B2 | 5/2011 | Bub et al. | |
| 2001/0004960 A1 * | 6/2001 | Ishii et al. | 203/3 |
| 2001/0025093 A1 * | 9/2001 | Ishizaki et al. | 526/210 |
| 2002/0087029 A1 | 7/2002 | Eck et al. | |
| 2002/0120085 A1 | 8/2002 | Matsumoto et al. | |
| 2003/0060661 A1 * | 3/2003 | Eck et al. | 562/600 |
| 2004/0116741 A1 * | 6/2004 | Nordhoff et al. | 562/600 |
| 2004/0157734 A1 | 8/2004 | Mertens et al. | |
| 2005/0204612 A1 | 9/2005 | Connemann et al. | |
| 2006/0029782 A1 | 2/2006 | Harren et al. | |
| 2006/0057389 A1 | 3/2006 | Reimann et al. | |
| 2008/0221277 A1 | 9/2008 | Walden et al. | |
| 2008/0280128 A1 | 11/2008 | Furno et al. | |
| 2008/0287616 A1 | 11/2008 | Balduf et al. | |
| 2009/0202805 A1 | 8/2009 | Furno et al. | |
| 2009/0227741 A1 | 9/2009 | Walden et al. | |
| 2010/0035757 A1 | 2/2010 | Furno et al. | |
| 2010/0036004 A1 | 2/2010 | Harren et al. | |
| 2010/0057027 A1 | 3/2010 | Furno et al. | |
| 2010/0209379 A1 | 8/2010 | Furno et al. | |
| 2011/0009272 A1 | 1/2011 | Wattebled et al. | |
| 2011/0028664 A1 | 2/2011 | Nordhoff et al. | |
| 2011/0046297 A1 | 2/2011 | Hengstermann et al. | |
| 2011/0105791 A1 | 5/2011 | Kuppinger et al. | |

FOREIGN PATENT DOCUMENTS

| | | | | |
|---|---|---|---|---|
| DE | 4401405 A1 | 7/1995 | | |
| DE | 19529348 A1 | 2/1997 | | |
| DE | 19718608 A1 | 11/1998 | | |
| DE | 19853064 A1 | 5/1999 | | |
| DE | 19848208 A1 | 4/2000 | | |
| DE | 10019381 A | 11/2001 | | |
| DE | 10149353 A1 | 7/2002 | | |
| DE | 10125599 A1 | 11/2002 | | |
| DE | 10138150 A1 | 2/2003 | | |
| EP | 0567207 A2 | 10/1993 | | |
| EP | 0695736 A1 | 2/1996 | | |
| EP | 0598229 B1 | 9/1996 | | |
| EP | 0974574 A1 | 1/2000 | | |
| EP | 1163201 A | 12/2001 | | |
| EP | 1234612 A2 | 8/2002 | | |
| EP | 1302485 A1 | 4/2003 | | |
| FR | 695631 | 12/1930 | | |
| GB | 141057 | 6/1921 | | |
| GB | 343832 | 2/1931 | | |
| GB | 346221 | 4/1931 | | |
| JP | 59074993 A * | 4/1984 | | C12P 7/06 |
| WO | 9905085 A1 | 2/1999 | | |
| WO | 0116346 A1 | 3/2001 | | |
| WO | WO 0116346 A1 * | 3/2001 | | |
| WO | 0144145 A1 | 6/2001 | | |
| WO | 0242418 A1 | 5/2002 | | |
| WO | 0242418 A2 | 5/2002 | | |
| WO | 02056812 A2 | 7/2002 | | |
| WO | 02090312 A1 | 11/2002 | | |
| WO | 03014172 A2 | 2/2003 | | |
| WO | 03082795 A2 | 10/2003 | | |
| WO | WO 03082795 A2 * | 10/2003 | | |
| WO | 2004029016 A1 | 4/2004 | | |
| WO | 2004035514 A1 | 4/2004 | | |
| WO | 2004037903 A2 | 5/2004 | | |
| WO | 2005054488 A2 | 6/2005 | | |

OTHER PUBLICATIONS

Translation of the International Preliminary Report on Patentability issued on Sep. 11, 2007 in PCT/EP2006/001830.

Bub et al., U.S. Appl. No. 131029,208, filed Feb. 17, 2011.

Danner et al., "Biotechnological Production of Acrylic Acid from Biomass," copyright 1998, Applied Biochemistry and Biotechnology, vol. 70-72, pp. 887-894, Humana Press Inc.

Sanseverino et al., "Detection of acrylic acid formation in Megasphaera elsdenii in the presence of 3-butynoic acid," copyright 1989, Applied Microbiology and Biotechnology, vol. 30, pp. 239-242.

Stochniol et al., U.S. Appl. No. 13/128,538, filed May 10, 2011.

Zanthoff et al., U.S. Appl. No. 13/060,599, filed Feb. 24, 2011.

* cited by examiner

WATER-ABSORBENT POLYMER STRUCTURES BASED ON RENEWABLE RESOURCES AND METHOD FOR PRODUCING SAID STRUCTURES

This application is a national stage application under 35 U.S.C. 371 of international application No. PCT/EP2006/001830 filed 28 Feb. 2006, and claims priority to German Application No. DE 10 2005 009 584.4 filed 28 Feb. 2005, the disclosure of which is expressly incorporated herein by reference.

BACKGROUND

The present invention relates to a process for the production of polymers, preferably water-absorbing polymer structures, by radical polymerization of acrylic acid, the water-absorbing polymer structures obtainable by this process, water-absorbing polymer structures which are based to at least about 25 wt. % upon partially neutralized acrylic acid, a composite, a process for the production of a composite, the composite obtainable by this process, the use of acrylic acid in the production of polymers, preferably in the production of water-absorbing polymer structures, a device for the production of acrylic acid, a process for the production of acrylic acid, and the acrylic acid obtainable by this process.

High demands are made of the purity of monomers which are used in the production of polymeric compounds. This is particularly the case if the polymers are so-called superabsorbent polymers. These polymers are capable of absorbing and thereby binding aqueous liquids to form a hydrogel. Superabsorbent polymers are, therefore, used in particular in hygiene articles such as diapers, incontinence articles, sanitary napkins, and the like for the absorption of body fluids. A comprehensive overview of superabsorbent polymers, their application, and their production is given by F. L. Buchholz and A. T. Graham (Editors) in "Modern Superabsorbent Polymer Technology", Wiley-VCH, N.Y., 1998.

Superabsorbent polymers may be produced from pure acrylic acid prepared by catalytic gas phase oxidation of propylene to acrolein, wherein the acrolein is then converted in a further catalytic gas phase oxidation to acrylic acid. Then the acrylic acid is further processed by the gaseous reaction mixture in water, distillation of the thus-obtained aqueous acrylic acid solution to obtain a crude acrylic acid, and further purification of the crude acrylic acid by means of distillation or crystallization.

It is a disadvantage of this process for production of acrylic acid that the temperatures between about 300° C. and about 450° C. applied in both steps lead to formation of oligomers and further undesired cracking products. This has the result that an undesirably large amount of compounds which are less volatile than acrylic acid, or compounds which are only separated from acrylic acid with difficulty, such as, for example, acetic acid, is formed. These compounds must generally be separated from the acrylic acid by distillation, which in turn leads to a further thermal stress on the acrylic acid and to the formation of dimers and oligomers which is linked therewith. A high content in acrylic acid dimers or acrylic acid oligomers is, however, disadvantageous, since these dimers or oligomers are incorporated into the polymer backbone during the production of superabsorbent polymers by radical polymerization of acrylic acid in the presence of crosslinkers. During the post-treatment of the surface of the polymer particles occurring after the polymerization, for example during a surface post-crosslinking, the polymerized-in dimers, however, are cleaved to form β-hydroxypropionic acid, which is dehydrated to form acrylic acid under the post-crosslinking conditions. A high content in dimeric acrylic acid in the acrylic acid used in the production of superabsorbent polymer therefore leads to increased content in acrylic acid monomers upon thermal treatment of the polymer, as occurs during the post-crosslinking.

Since the soluble parts, in particular the acrylic acid monomers, in superabsorbent polymers can cause skin irritation, the use of these polymers in hygiene articles requires a particularly low content in extractable components.

Also other, often toxic compounds are still comprised in the acrylic acid obtainable by catalytic gas phase oxidation. These impurities include, in particular, aldehydes, which have a disruptive effect upon the course of polymerization, with the result that the polymers comprise considerable amounts of soluble components.

Acrylic acids produced in previous ways from propylene comprise not inconsiderable amounts of ketones having double bonds, in particular protoanemonine (PTA). This compound can, on contact with skin, cause signs of poisoning, such as, for example, reddening, itching, or blister formation. Superabsorbent polymers which comprise large amounts of PTA as soluble components are therefore of concern from a dermatological viewpoint. Furthermore, PTA disrupts the polymerization, as described in US-A-2002/0120085. This leads to the obtaining of superabsorbent polymers with less good absorption, transport, and retention properties for body fluids, so that when using superabsorbent polymers of this type in hygiene articles such as diapers or sanitary napkins, wearer comfort is worsened, for example by "leakage".

Some processes have already been described in the state of the art, with which the content in the above-mentioned compounds, in particular of aldehydes or PTA in acrylic acid obtained by gas phase oxidation of propylene can be reduced.

DE-A-101 38 150 suggests, in order to reduce the amount of aldehyde in the acrylic acid, bringing this into contact with an aldehyde trapper, in order to convert the aldehydes into high-boiling compounds, which can then be separated by means of distillation.

Various methods have been proposed in the state of the art for the removal of PTA, such as the addition of a nitrous acid salt, of nitrogen oxide or of nitrobenzene (JP 81-41614) or the addition of one or more para-phenylene diamines (EP-A-567 207) to the acrylic acid.

The disadvantage of the above-described processes for reducing the amount of aldehydes and ketones in acrylic acid is, however, among others, that, in so far as the impurity content of the acrylic acid is not known exactly, these reagents must be used in excess for the purpose of as complete a removal as possible of impurities from the acrylic acid. On the one hand, reagents which are reactive to the acrylic acid must be added. The portion of these reagents which is not converted must then be removed again. Reagents which are not removed are comprised in the superabsorbent polymer obtained from such an acrylic acid as soluble components, which can come into contact with the skin of the hygiene article wearer when the superabsorbent polymers are used in hygiene articles. Furthermore, the processes known from the prior art for removal of aldehydes in ketones from acrylic acid only very seldom remove these impurities completely.

In addition to the disadvantages which are traced back to impurities in the acrylic acid used in the production of superabsorbent polymers, known superabsorbent polymers also have the disadvantage that, unless they at least partially comprise natural polymers, such as celluloses, they are hardly based upon renewable raw materials. While it is successful to produce many of the components used in hygiene articles, in particular in disposable diapers, from biological starting materials, replacement of the superabsorbent polymers based upon cross-linked polyacrylates by natural superabsorbent polymers, such as cross-linked, derivatized starches or celluloses, is generally associated with significant losses in respect of the absorbent properties. This mostly leads to the necessity of using considerably more of the absorbents based upon natural polymers, simply in order to approach the same absorbent properties in a hygiene article. This is disadvantageous, because the hygiene articles become more voluminous and heavier, which significantly restricts wearing comfort and leads to a larger waste volume, which, in addition to dumping space or combustion expenditure also requires greater transport capacity for the removal of waste. All of this has a disadvantageous effect upon the environmental friendliness of the absorbers based upon natural polymers.

SUMMARY

The object of the present invention was to overcome the disadvantages arising from the state of the art.

In particular, the present invention had the object of making available polymers, in particular superabsorbent polymers, which have a particularly low content in extractable, possibly toxic components.

Furthermore, the object of the present invention was to provide polymers, in particular superabsorbent polymers, which are environmentally friendly and still have excellent application properties. In particular, it was desired to provide superabsorbent polymers with improved environmental friendliness while retaining the same good absorbent properties.

In addition, it was an object of the present invention to improve the environmental friendliness of further processing products comprising the polymers according to the invention, such as composites in general and hygiene articles in particular, without the desired functions, such as absorbent capability, wearing comfort, and simple producibility of these further processing products suffering.

It was also an object of the present invention to provide a process for preparing polymers of this type and the monomers suitable for their production, whereby this process should take place as far as possible without the use of reactive compounds for removal of impurities from the monomers used in the preparation of the polymers.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

In addition, an object of the present invention was to suggest a process and a device for the production of monomers and polymers, which can be integrated with as little conversion expenditure as possible into existing industrial manufacturing processes and devices.

FIGURES

The foregoing and other features, aspects, and advantages of the present invention will become better understood with regard to the following description, appended claims, and accompanying drawings where:

DETAILED DESCRIPTION

Figure 1:
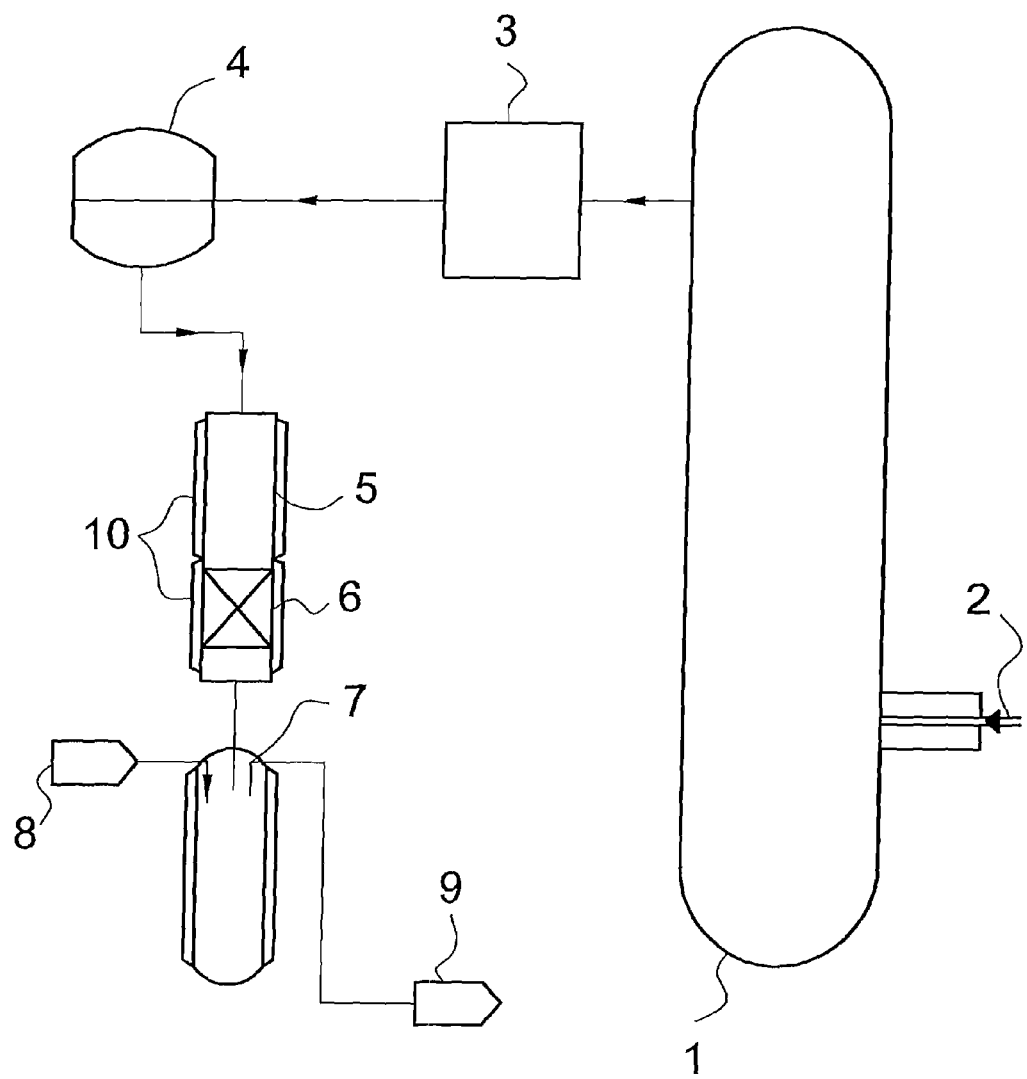
FIG. 1 shows a device according to the invention for production of acrylic acid, in which a dehydration occurs in the gas phase.

A contribution to the solution of the above-mentioned objects may be provided by a process for the production of polymers by radical polymerization of acrylic acid, whereby the acrylic acid has been obtained by a synthesis process which comprises the following, preferably first, process step:
   splitting of an organic material by means of an enzyme or at least one component of an enzyme.

By "splitting of an organic material by means of an enzyme or at least one component of an enzyme" is understood a process, in which an organic material is split either by means of microorganisms, which are present in the form of intact, functional cells, or by means of enzymes isolated from microorganisms. The isolated enzymes could be dissolved in a suitable reaction medium. It is also conceivable, however, to immobilize the enzymes on a substrate, for example on the surface of a porous matrix, and to then allow the reaction medium to flow respectively along the substrate or through the porous matrix.

The term "splitting" thus comprises both a splitting of an optionally polymeric organic material, such as, for example, celluloses or starches, into individual oligomers or monomers as well as the further splitting of the monomers into smaller fragments. Hence, the splitting of the organic materials occurs by means of fermentation.

Polymers according to the invention may be water-absorbing polymers, which are obtainable by a process comprising the following process steps:
   i) polymerizing the acrylic acid in the presence of a cross-linker to form a polymer gel;
   ii) optionally, comminuting the polymer gel;
   iii) drying of the polymer gel to obtain water-absorbing polymer structures; and
   iv) optionally, surface post-treatment, or surface post-crosslinking, of the water-absorbing polymer structure.

These water-absorbing polymer structures are preferably based upon:
   ($\alpha$1) from about 20 to about 99.999 wt %, or from about 55 to about 98.99 wt %, or from about 70 to about 98.79 wt % acrylic acid,
   ($\alpha$2) from 0 wt % to about 80 wt %, or from 0 wt % to about 44.99 wt %, or from about 0.1 wt % to about 44.89 wt % polymerized, monoethylenically unsaturated monomers copolymerizable with acrylic acid,
   ($\alpha$3) from about 0.001 to about 5 wt %, or from about 0.01 wt % to about 3 wt %, or from about 0.01 wt % to about 2.5 wt % of one or more crosslinker,
   ($\alpha$4) from 0 wt % to about 50 wt. %, or from 0 wt % to about 25 wt. %, or from about 0.1 to about 5 wt % of a water-soluble polymer,
   ($\alpha$5) from 0 wt % to about 20 wt %, or from about 2.5 to about 15 wt %, or from about 5 wt % to about 10 wt % water, and (α6) from 0 wt % to about 20 wt %, or from 0 wt % to about 10 wt %, or from about 0.1 wt % to about 8 wt % of one or more additives, whereby the sum of the weight amounts (α1) to (α6) is 100 wt %.

The acrylic acid monomers (α1) can be partially or fully, preferably partially neutralized. Preferably, acrylic acid monomers are neutralized to at least about 25 mol %, or to at least about 50 mol %, or from about 50 mol % to about 80 mol %. In this context, reference is made to DE 195 29 348 A1. The neutralization can also occur partially or fully after the polymerization. Furthermore, the neutralization can occur with alkali metal hydroxides, alkaline earth metal hydroxides, ammonia, carbonates, and bicarbonates. In addition, every further base is conceivable which forms a water-soluble salt with the acid. A mixed neutralization with different bases is also conceivable. Neutralization with ammonia and alkali metal hydroxides is an embodiment, with sodium hydroxide and with ammonia is another embodiment.

Acrylamides and methacrylamides may be used as monoethylenically unsaturated monomers (α2) copolymerizable with acrylic acid.

(Meth)acrylamides may include, in addition to acrylamide and methacrylamide, alkyl-substituted (meth)acrylamides or aminoalkyl-substituted derivatives of (meth)acrylamide, such as N-methylol(meth)acrylamide, N,N'-dimethylamino (meth)acrylamide, dimethyl(meth)acrylamide, or diethyl (meth)acrylamide. Possible vinylamides are, for example, N-vinylamides, N-vinylformamides, N-vinylacetamides, N-vinyl-N-methylacetamides, N-vinyl-N-methylformamide, vinyl pyrrolidone.

Monoethylenically unsaturated monomers (α2) copolymerizable with acrylic acid may include monomers that are dispersible in water. Monomers which are dispersible in water may include acrylic acid esters and methacrylic acid esters, such as methyl(meth)acrylate, ethyl(meth)acrylate, propyl(meth)acrylate or butyl(meth)acrylate, as well as methylpolyethyleneglycol(meth)acrylate, methylpolyethyleneglycol allylether, vinyl acetate, styrene, and isobutylene.

Crosslinker (α3) that may be used include those compounds that are mentioned in WO 2004/037903 A1. Among these crosslinkers, water-soluble crosslinkers may be used. Crosslinkers may include N,N-methylenebisacrylamide, polyethyleneglycol di(meth)acrylate, triallylmethylammonium chloride, tetraallylammonium chloride, as well as allylnonaethyleneglycol acrylate prepared with 9 moles of ethylene oxide per mole of acrylic acid.

As water-soluble polymers (α4), water-soluble polymers, such as partially or fully saponified polyvinylalcohol, polyvinylpyrrolidone, starches or starch derivatives, polyglycols, or polyacrylic acids can be comprised, or polymerized into the polymer structures. The molecular weight of these polymers may not be critical, as long as they are water-soluble. Water-soluble polymers may include starches or starch derivatives or polyvinyl alcohol. The water-soluble polymers such as polyvinyl alcohol can also serve as a graft basis for the monomers to be polymerized.

One or more additives (α6) such as or suspending agents, odor binders, surface active agents, or anti-oxidants as well as those additives which may be used in the production of the polymer structure (initiators, etc.) may be included in the polymer structures.

In another embodiment of the water-absorbing polymer structures according to the invention, these may be based to at least about 50 wt %, or to at least about 70 wt %, or yet to at least about 90 wt % upon acrylic acid monomers that is neutralized to at least about 20 mol %, or to at least about 50 mol %, or within a range from about 60 mol % to about 85 mol %.

Polymer structures may include fibers, foams, or particles.

Polymer fibers may be dimensioned so that they can be incorporated into yarns for textiles and also directly into textiles. The polymer fibers may have a length within the range from about 1 mm to about 500 mm, or from about 2 mm to about 500 mm, or from about 5 to about 100 mm and a diameter within the range from about 1 denier to about 200 denier, or from about 5 to about 100 denier, or from about 5 to about 60 denier.

Polymer particles may be dimensioned so that they have an average particle size according to ERT 420.2-02 within the range from about 10 μm to about 3000 μm, or from 20 μm to about 2000 μm, or from about 150 μm to about 850 μm. The polymer particles may be based to at least about 50 wt %, or to at least about 75 wt % upon particles with a particle size within a range from about 300 μm to about 600 μm.

More details concerning the production of water-absorbing polymer structures based upon acrylic acid may be found in F. L. Buchholz and A. T. Graham (Editors) in "Modern Superabsorbent Polymer Technology", Wiley-VCH, N.Y., 1998. The disclosure of this document concerning the production of water-absorbing polymers based upon acrylic acid, in particular with respect to the monomers to be used, the polymerization conditions, the processing of the polymer gels, and the surface modification possibilities.

As organic material, any material may be used in the process according to the invention which can be split to form finally 3-hydroxypropionic acid (β-hydroxypropionic acid) with catalytic assistance from enzymes, for example in a fermentation process, whereby this splitting can optionally occur in several steps. As organic material, natural mixtures can be, for example, considered, such as malt extract, oatmeal or milk powder, or pure, defined carbohydrates, in particular polysaccharides, for example raffinose, starches, celluloses, glycogens or dextrins, disaccharides, for example saccharose, lactose or maltose, and monosaccharides, preferably hexoses such as, for example, galactose, xylose, glucose, galactose or fructose, or also sugar alcohols, whereby glucose is particularly preferred as carbon source. The organic material may be based to at least about 75 wt %, or to at least about 85 wt %, or to at least about 95 wt % upon optionally polymerized hexoses, or polymerized glucose.

The organic material may be a naturally occurring organic material. A naturally occurring organic material may be a material which has come into being on the earth in a natural way, by use of photosynthesis, by biosynthesis (anabolism) within the last 4000 years, or within the last 1000 years, or within the last 10 years, or within the last 12 months.

The splitting of the organic materials may lead to formation of β-hydroxypropionic acid, whereby glucose- or xylose-comprising materials may be used as organic material and the splitting of the glucose or of the xylose occurs by means of a fermentation process. Microorganisms, which are capable of splitting suitable organic starting materials to form β-hydroxypropionic acid, may be incubated in a suitable culture medium, so that they grow to a desired cell density with formation of β-hydroxypropionic acid. General information for a large scale process can, for example, be found in the "Manual of Industrial Microbiology and Biotechnology", 2$^{nd}$ Edition, A. L. Demain and J. E. Davies (Editors), ASM Press, as well as "Principles of Fermentation Technology", P. F. Stanbury and A. W. Whitaker (Editors), Pergamon.

Generally, in a fermentation process, a nutrient solution situated in a fermentation tank, comprising carbon sources, nitrogen sources, salts, and further substances necessary for the nutrition of microorganisms may be inoculated with suitable microorganisms. The microorganisms may then be cultivated in this nutrient medium until a given density is reached. A part of the thus-obtained broth may then be transferred into a second fermentation tank, in which likewise a suitable nutrient medium is placed, whereby the second fermentation tank may be larger than the first fermentation tank. In this second fermentation tank, the microorganisms may grow until a desired cell density is reached or until a desired β-hydroxypropionic acid concentration in the nutrient medium is reached. Such a fermentation process may also be carried out continuously, as described, for example, in DE-A-197 18 608 for the preparation of lactic acid. With regard to the microorganisms to be used in the preparation of β-hydroxypropionic acid from carbohydrates, these can be found in WO-A-02/42418.

After sufficient amounts of β-hydroxypropionic acid have been formed in the cause of the fermentation, the β-hydroxypropionic acid may be isolated by any purification process known to the skilled person. Thus, for example, sedimentation, filtration, or centrifugation processes can be used in order to separate the microorganisms. The hydroxypropionic acid can be isolated from the β-hydroxypropionic acid-comprising nutrient solution which has been removed from the microorganisms, by extraction, distillation, or ion exchange.

The purification of the β-hydroxypropionic acid from the nutrient solution may occur continuously according whereby it may also carry out the fermentation continuously, so that the whole process, from the enzymatic splitting of the organic material to form β-hydroxypropionic acid to the purification of the β-hydroxypropionic acid from the fermentation broth may be carried out continuously. In the continuous purification of the β-hydroxypropionic acid from the fermentation broth, this may be conducted continuously via a device for separation of the microorganisms used in the fermentation, preferably via a filter with an opening size within a range from about 20 kDa to about 200 kDa, in which a solid/liquid separation takes place. The use of a centrifuge, or a suitable sedimentation device or a combination of these devices is also conceivable, whereby it is particularly preferred to separate at least a part of the microorganisms first by sedimentation and then to conduct the fermentation broth which has been at least partially freed from the microorganisms to an ultrafiltration or a centrifugation device. The retentate may be conducted back into the second fermentation tank. Alternatively, the retentate can be conducted away and optionally discarded.

The fermentation product, enriched with respect to its β-hydroxypropionic acid amount, may be conducted after the separation of the microorganisms to a multi-step separating system. In this separating system, multiple separating steps arranged one after the other are provided, out of which respectively back-conducting-lines lead, which are conducted back to the second fermentation tank. Furthermore, lines lead out of the respective separation steps. The individual separation steps can operate according to the principle of electrodialysis, reverse osmosis, ultrafiltration, or nanofiltration. There may be membrane separating devices in the individual separating steps. The choice of the individual separating steps may be made depending upon the type and amount of the fermentation side-products and substrate residues.

In addition to the separation of the β-hydroxypropionic acid by means of electrodialysis, reverse osmosis, ultrafiltration, or nanofiltration, in the course of which an aqueous β-hydroxypropionic acid solution may be obtained as end product, the β-hydroxypropionic acid may also be separated from the fermentation solution that has been removed from the micro organisms by extraction processes, whereby pure β-hydroxypropionic acid may finally be obtained. In the separation of the β-hydroxypropionic acid by extraction, ammonium compounds or amines may be added to the fermentation solution in order to form an ammonium salt of the β-hydroxypropionic acid. This ammonium salt may then be separated from the fermentation solution by adding an organic extraction agent and then heating the thus-obtained mixture, whereby the ammonium salt is enriched in the organic phase. The β-hydroxypropionic acid may then be isolated from this phase to obtain pure β-hydroxypropionic acid, for example by further extraction steps. Further details concerning this separation process can be found in WO-A-02/090312, whose disclosure limited to the separation of β-hydroxypropionic acid from fermentation solutions is hereby introduced as reference.

Depending upon the type and means of separation of the β-hydroxypropionic acid from the fermentation solution, either an aqueous β-hydroxypropionic acid solution comprising from about 2 to about 90 wt %, or from 7.5 wt % to about 50 wt %, or from about 10 wt % to 25 wt % β-hydroxypropionic acid, or pure β-hydroxypropionic acid, is obtained.

According to an embodiment of the process according to the invention for the production of polymers by means of radical polymerization of acrylic acid, the synthesis process of the acrylic acid comprises, in addition to the above-described process step of enzymatic splitting of an organic material to form β-hydroxypropionic acid, a further process step, in which the β-hydroxypropionic acid is catalytically dehydrated to form acrylic acid. In this dehydration step, either the pure β-hydroxypropionic acid isolated from the fermentation solution, or the aqueous β-hydroxypropionic acid solution isolated from the processing of the fermentation solution may be used, whereby this is optionally concentrated before the dehydration, for example by distillation, optionally in the presence of a suitable entrainer.

The dehydration may be carried out in the liquid phase or in the gas phase. The dehydration may occur in the presence of a catalyst, whereby the type of the catalyst used may be dependent upon whether a gas phase or a liquid phase reaction is carried out.

Dehydration catalysts may be acidic as well as basic catalysts. Acidic catalysts may be advantageous because of the low tendency to form oligomers. The dehydration catalyst may be used as a homogeneous as well as a heterogeneous catalyst. If the dehydration catalyst is present as a heterogeneous catalyst, it is preferred that the dehydration catalyst is in contact with a carrier x., as carrier x may be considered all solids that are known to the skilled person. In this context, the solid has suitable pore volumes, which are suited for a good binding and taking up of the dehydration catalyst. In addition, total pore volumes according to DIN 66133 within a range from about 0.01 ml/g to about 3 ml/g, or within a range from about 0.1 ml/g to about 1.5 ml/g. In addition, the solids suitable as carrier x have a surface area within the range from about 0.001 $m^2/g$ to about 1000 $m^2/g$, or within the range from about 0.005 $m^2/g$ to about 450 $m^2/g$, or within the range from about 0.01 $m^2/g$ to about 300 $m^2/g$ according to BET test according to DIN 66131. A bulk good, which has an average particle diameter within the range from about 0.1 mm to about 40 mm, or within the range from about 1 mm to about 10 mm, or within the range from about 1.5 mm to about 5 mm, may be used as carrier for the dehydration catalyst. The wall of the dehydration reactor may also serve as carrier. Furthermore, the carrier may itself be acidic, or basic, or an acidic or basic dehydration catalyst may be applied to an inert carrier. Application techniques may include immersion, or impregnation, or the incorporation into a carrier matrix.

Carrier x that may also have dehydration catalyst properties, may be natural or synthetic silicate materials, such as, in particular, mordenite, montmorillonite, acidic zeolites, carrier materials supporting mono-, di- or polybasic inorganic acids, such as phosphoric acids, or acidic salts of inorganic acids, such as oxidic or silicate materials, for example $Al_2O_3$, $TiO_2$, oxides and mixed oxides, such as, for example, gamma-$Al_2O_3$ and ZnO—$Al_2O_3$-mixed oxides of heteropolyacids.

The carrier x may consist at least partially of an oxidic compound. Such oxidic compounds should have at least one of the elements Si, Ti, Zr, Al, P or a combination of at least two thereof Such carriers may also function as dehydration catalysts through their acidic or basic properties. A preferred class of compounds which function both as carrier x and as a dehydration catalyst comprises silicon-aluminium-phosphorus oxides. Basic materials that may function as both a dehydration catalyst and as carrier x may comprise alkali metal, alkaline earth metal, lanthanum, lanthanide, or a combination of at least two thereof in their oxidic form. Such oxidic or basic dehydration catalysts are commercially obtainable from Degussa AG and from Sildchemie AG. Ion exchangers represent a further class. These may also be present in both basic and acidic form.

As homogeneous dehydration catalysts may be considered in particular inorganic acids, such as phosphorous-comprising acids, or phosphoric acids, these inorganic acids may be immobilized on the carrier x by immersion or impregnation.

The use of heterogeneous catalysts has proven particularly successful, in particular in gas phase dehydration. In liquid phase dehydration, however, both homogeneous and heterogeneous dehydration catalysts may be used.

In addition, a dehydration catalyst may be used with an $H_0$ value within a range from +1 to −10, or within a range from +2 to −8.2, or in the liquid phase dehydration within a range from +2 to −3 and in the gas phase dehydration within a range from −3 to −8.2. The $H_0$ value corresponds to the acidic function according to Hammett and can be determined by the so-called amine titration and use of indicators or by absorption of a gaseous base—see "Studies in Surface Science and Catalytics", vol. 51, 1989: "New Solid Acids and Bases, their Catalytic Properties", K. Tannabe et. al. Further details on the production of acrolein from glycerine can also be found in DE 42 38 493 C1.

A porous carrier body that has been brought into contact with an inorganic acid, or with phosphoric acid, or with superacids such as, for example, sulfatized or phosphatized zirconium oxide, and which is based to at least about 90 wt %, or to at least about 95 wt %, or to at least about 99 wt % upon a silicon oxide, such as $SiO_2$, may be used as an acidic solid state catalyst. The bringing into contact of the porous carrier body with the inorganic acid may occur by impregnation of the carrier body with the acid, whereby this acid, in an amount within a range from about 10 wt % to about 70 wt %, or within a range from about 20 wt % to about 60 wt %, or within a range from about 30 wt % to about 50 wt %, based upon the weight of the carrier body, may be brought into contact with the carrier body and then dried. After the drying, the carrier body may be heated in order to fix the inorganic acid, to a temperature within a range from about 300° C. to about 600° C., or within a range from about 400° C. to about 500° C.

The dehydration may be carried out in the gas phase. To this end, conventional apparatuses, as known to the skilled person for gas phase reactions, for example pipe reactors, may be used. Pipe bundle heat exchangers and reactors which comprise thermoplates as heat exchangers may be used.

According to an embodiment of the gas phase dehydration, pure β-hydroxypropionic acid may be introduced into a reactor comprising one of the above-mentioned solid bed catalysts. According to another embodiment, the β-hydroxypropionic acid may be introduced into the reactor in the form of an aqueous solution comprising from about 2 wt % to about 80 wt %, or from about 5 wt % to 50 wt %, or from about 10 wt % to about 25 wt % β-hydroxypropionic acid, respectively based upon the total weight of the aqueous solution. The pressure and temperature conditions inside the reactor may be selected so that the β-hydroxypropionic acid or the aqueous solution respectively is present in gaseous form upon entering the reactor.

The dehydration in the gas phase may occur within a temperature range between about 200° C. and about 400° C., or between about 250° C. and about 350° C. The pressure inside the reactor during the gas phase dehydration preferably may lie within a range from about 0.1 bar to about 50 bar, or within a range from about 0.2 bar to about 10 bar, or within a range from about 0.5 bar to about 5 bar.

The amount of β-hydroxypropionic acid introduced into the reactor for the gas phase dehydration preferably may lie within a range from about 10 vol % to about 100 vol %, or within a range from about 20 vol % to about 100 vol %, or within a range from about 30 vol % to about 100 vol %.

The dehydration may be carried out in the liquid phase. The liquid phase dehydration may likewise be carried out in all apparatuses known to the skilled person, in which a fluid may be heated to a desired reaction temperature, whereby the apparatus may be pressurized to a sufficient pressure to keep the reaction components liquid under the desired temperature conditions.

The process of liquid phase dehydration comprises a first process step, in which pure β-hydroxypropionic acid, or an aqueous solution comprising from about 5 wt % to 100 wt %, or from about 20 wt % to 100 wt %, or from about 50 wt % to 100 wt % of β-hydroxypropionic acid, based upon the total weight of the aqueous solution, is introduced into a reactor. The pressure and temperature conditions inside the reactor may be selected so that the β-hydroxypropionic acid or the aqueous solution respectively is in liquid form upon entry into the reactor. According to an embodiment of the process according to the invention, in which a dehydration is carried out in the liquid phase, the β-hydroxypropionic acid or the aqueous solution respectively inside the dehydration reactor may be conducted over a catalyst bed in such a way that the liquid phase ripples over the surface of the catalyst particles. A process of this type can, for example, be carried out in a ripple bed reactor.

The dehydration in the liquid phase preferably occurs within the temperature range between about 200° C. and about 350° C., or between about 250° C. and about 300° C. The pressure inside the reactor during the liquid phase dehydration preferably lies within a range from about 1 bar to about 50 bar, or within a range from about 2 bar to about 25 bar, or within a range from about 3 bar to about 10 bar.

The catalysis of the dehydration may occur homogeneously or heterogeneously, in both the gas phase dehydration and in the liquid phase dehydration.

In the homogeneous catalysis, the catalyst, which may be an inorganic acid, such as, for example, phosphoric acid or sulphuric acid, may first be brought into contact with the pure β-hydroxypropionic acid or with the aqueous solution comprising the β-hydroxypropionic acid. The thus-obtained composition may then be introduced into the reactor and converted into acrylic acid under the desired pressure and temperature conditions. It is also conceivable to introduce the inorganic acid into the reactor independently of the β-hydroxypropionic acid or the aqueous solution respectively. In this case, the reactor comprises at least two feed lines, one for the β-hydroxypropionic acid or the aqueous solution comprising the β-hydroxypropionic acid respectively and one for the catalyst. If the dehydration in the liquid phase is carried out in a ripple bed reactor, the catalyst, together with the β-hydroxypropionic acid or the aqueous solution comprising the β-hydroxypropionic acid respectively may be introduced in the head area of the reactor.

In the heterogeneous catalysis, the catalyst may be in the form of a solid substrate in the reaction space, for example in the form of a solid bed fill, in the form of plates coated with catalyst, preferably thermoplates, which may be arranged inside the reactor, or in the form of reactor walls coated with catalyst. Possible reactors are, for example, described in DE-A-198 48 208, DE-A-100 193 81, and EP-A-1 234 612. In the case of heterogeneous catalysis, porous carrier bodies brought into contact with inorganic acids, impregnated, are preferred as catalysts. The β-hydroxypropionic acid or the aqueous solution comprising the β-hydroxypropionic acid respectively may then be brought into contact in vapor or liquid form with the surface of the solid catalyst material.

As reaction mixture which is obtained following the dehydration, either an aqueous acrylic acid solution, which comprises no catalyst components (such a one is obtained in the case of a heterogeneously catalysed dehydration) or an aqueous acrylic acid solution which comprises catalysts (such a one is obtained in the case of a homogeneously catalysed dehydration) is obtained. Furthermore, the aqueous acrylic acid solution may be present in liquid form (in so far as the dehydration is carried out in the liquid phase) or gaseous (in so far in as the dehydration is carried out in the gas phase).

This aqueous acrylic acid solution may be purified by any purification process known to the skilled person, which is conventionally used in the purification of impure acrylic acid obtained by catalytic gas phase oxidation of propylene.

If the dehydration is carried out in the gas phase, it is preferred that the acrylic acid is first condensed to obtain an aqueous acrylic acid solution. To this end, any condensation process known to the skilled person may be used, for example a fractionated condensation, as described in WO-A-2004/035514, WO-A-03/014172, or EP-A-1 163 201, or a total condensation, as described in EP-A-0 695 736. It is also conceivable to add additional solvent, in particular water, during the condensation, in order to absorb the acrylic acid as fully as possible.

The aqueous acrylic acid solution obtained after the condensation or, in the case of liquid phase dehydration, the obtained aqueous acrylic acid solution may then be freed from water and other impurities in further purification steps. To this end, first the water may be removed in the presence of an entrainer by azeotropic distillation, as described, for example, in DE-A-198 53 064. The use of high-boiling organic solvents for absorption of the acrylic acid is also conceivable, as disclosed in, for example, EP-A-0 974 574. In addition to these distillative processes, membranes can also be used for the removal of water, as suggested in, for example, DE-A-44 01 405. Also conceivable is a purification by crystallization processes of the aqueous acrylic acid solution obtained from the liquid phase dehydration or by condensation, whereby optionally a separation means, for example toluene, can be added before the crystallization to the aqueous acrylic acid solution to be purified.

The acrylic acid obtained after the removal of water may be further purified in further process steps. In this way, high-boiling impurities still comprised may be removed by further distillation steps. It is, however, preferred if the acrylic acid obtained after the removal of water may be further purified by crystallization processes, as described, for example, in DE-A-101 49 353. Before the crystallization, the acrylic acid which is to be purified may also be brought into contact with a separating agent, such as toluene.

After the purification of the acrylic acid-comprising composition obtained in the dehydration, an acrylic acid is obtained that is based to at least about 99 wt %, or to at least about 99.5 wt %, or to at least about 99.9 wt % upon acrylic acid.

According to an embodiment of the process according to the invention for the production of polymers by radical polymerization of acrylic acid, the synthesis process of the acrylic acid comprises the following process steps:
  splitting of a carbohydrate by means of an enzyme or at least one component of an enzyme to form β-hydroxypropionic acid, preferably in a fermenter;
  isolating the β-hydroxypropionic acid from the fermentation broth to obtain an aqueous β-hydroxypropionic acid solution, whereby the isolation can optionally be achieved by bringing into contact the fermentation solution freed from the microorganisms with an amine, extraction of the thus-obtained β-hydroxypropionic acid salt, and distillative purification of the extract;
  heterogeneous dehydration of the β-hydroxypropionic acid in the gas phase or in the liquid phase;
  condensating the gaseous reaction mixture to obtain an aqueous acrylic acid solution; and
  optionally adding a separating agent, such as toluene, to the aqueous acrylic acid solution and separation of the acrylic acid by means of crystallization.

According to another embodiment of the process according to the invention for the production of polymers by radical polymerization of acrylic acid, the synthesis process of the acrylic acid comprises the following process steps:
  splitting of a carbohydrate by means of an enzyme or at least one component of an enzyme to form β-hydroxypropionic acid, preferably in a fermenter;
  isolating the β-hydroxypropionic acid from the fermentation broth to obtain a pure β-hydroxypropionic acid, whereby the isolation can be achieved optionally by bringing into contact the fermentation solution freed from the microorganisms with an amine, extraction of the thus-obtained β-hydroxypropionic acid salt, and distillative purification of the extract;
  heterogeneous dehydration of the β-hydroxypropionic acid in the gas phase or in the liquid phase;
  condensing the gaseous reaction mixture to obtain an aqueous acrylic acid solution;
  optionally adding a separating agent, such as toluene, to the aqueous acrylic acid solution and separation of the acrylic acid by means of crystallization.

According to a particular embodiment of the process according to the invention for production of polymers by radical polymerization of acrylic acid, at least about 80 wt %, or at least about 90 wt %, or at least about 95 wt % of the acrylic acid monomers used in the production of the polymers have been obtained by the above-described synthesis process comprising the process step of the splitting of an organic material by means of an enzyme or at least one component of an enzyme.

After the acrylic acid has been purified according to the above-described purification process from the compositions obtained after the dehydration, the radical polymerization of the acrylic acid monomers may occur by means of polymerization processes known to the skilled person. If the polymers are cross-linked, partially neutralized polyacrylates, reference is made regarding the exact procedure to the third chapter (page 69 et seq.) in "Modern Superabsorbent Polymer Technology", F. L. Buchholz and A. T. Graham (Editors), Wiley-VCH, N.Y., 1998.

A contribution to the solution of the above-mentioned objects may also be made by water-absorbing polymer structures obtainable by radical polymerization of the acrylic acid obtainable by the above-described synthesis process in the presence of cross-linkers.

A contribution to the solution of the above-mentioned objects may also be made by water-absorbing polymer structures that are based to at least about 25 wt %, or to at least about 50 wt %, or to at least about 75 wt %, or to at least about 95 wt % upon acrylic acid, whereby at least about 80 wt %, or at least about 90 wt %, or at least about 95 wt % of the acrylic acid monomers used for the production of the water-absorbing polymer structures have been obtained by a synthesis process which comprises the process step of the splitting of an organic material by means of an enzyme or at least one component of an enzyme.

According to another embodiment of the water-absorbing polymer structures according to the invention, these may be based to at least about 25 wt %, or to at least about 35 wt %, or to at least about 45 wt % upon natural, biodegradable polymers, preferably upon carbohydrates such as, for example, celluloses or starches.

The water-absorbent polymer structures may have at least one of the following properties:
  a CRC value (CRC=Centrifugation Retention Capacity) determined according to ERT 441.2-02 (ERTM=Edana Recommended Test Method) of at least about 20 g/g, or at least about 25 g/g, or at least about 30 g/g, whereby a CRC value of about 60 g/g, or about 50 g/g, is not exceeded;
  an absorption under a pressure of 20 g/cm² determined according to ERT 442.2-02 of at least about 16 g/g, or at least about 18 g/g, or at least about 20 g/g, whereby a value of about 50 g/g, or about 40 g/g, is not exceeded.

A further contribution to the solution of the above mentioned objects is made by water-absorbing polymer structures, which may be characterized by the following properties:
  (β1) the polymer structure is based to at least about 25 wt %, or to at least about 50 wt %, or to at least about 75 wt %, or to at least about 95 wt % on acrylic acid, whereby at least about 80 wt %, or at least about 90 wt %, or at least about 95 wt % of the acrylic acid monomers used in the preparation of the water-absorbing polymer structures has been obtained by a synthesis process which comprises the process step of splitting an organic material by means of an enzyme or at least one component of an enzyme;
  (β2) the polymer structure has a biodegradability determined according to the modified Sturm Test according to Appendix V of Guideline 67/548/EWG after 28 days of at least about 25 wt %, or at least about 35 wt %, or at least about 45 wt %, whereby a value of at most from about 75 wt % to about 95 wt % as upper limit is generally not exceeded;
  (β3) the polymer structure has a CRC value determined according to ERT 441.2-02 of at least about 20 g/g, or at least about 25 g/g, or at least about 30 g/g, whereby a CRC value of about 60 g/g as upper limit is generally not exceeded.

In a further aspect of the polymer structure described in the previous paragraph, the polymer structure may have at least properties β1 and β2. All further developments given in this text for the polymer structure are also valid for the polymer structure of this paragraph.

Another contribution to the solution of the above-mentioned objects may be made by water-absorbing polymer structures that may be based to at least about 10 wt %, or at least about 25 wt %, or at least about 50 wt %, or at least about 75 wt %, or at least 80 wt %, based upon the polymer structure, upon acrylic acid and which are characterized by the following properties:
  (ε1) the polymer structure has a sustainability factor of at least about 10, or at least about 20, or at least about 50, or at least about 75, or at least about 85, or at least about 95;
  (ε2) the polymer structure has a biodegradability determined according to the modified Sturm Test according to Appendix V of Guideline 67/548/EWG after 28 days of at least about 25%, or at least about 35%, or at least about 45%, whereby a value of at most about 75 wt % to about 95 wt % as upper limit is generally not exceeded;
  (ε3) the polymer structure has a CRC value determined according to ERT 441.2-02 of at least about 20 g/g, or at least about 25 g/g, or at least about 29 g/g, whereby a CRC value of about 60 g/g as upper limit is generally not exceeded.

In another embodiment of the polymer structure described in the previous section, this polymer structure may have at least properties ε1 and ε2. All further developments given in this text for the polymer structure are also valid for the polymer structure of this paragraph.

In some cases, the above-mentioned upper limits may also be up to about 10% or up to about 20% lower. It is an embodiment for the polymer structures described in the two previous sections that these may be based, in addition to the acrylic acid, upon a di- or polysugar. These di- or polysugars may be present as a further component of the polymer structure in an amount of at least about 1 wt %, or at least about 5 wt %, or at least about 15 wt %, based upon the polymer structure, so that the sum of the wt % of the components of the water-absorbing polymer structure is 100 wt %. Sugars of these types may be poly-chain sugars, which may have a number average molecular weight determined by means of gel permeation chromatography and light scattering within the range from about 10,000 g/mol to about 1,000,000 g/mol, or within the range from about 50,000 g/mol to about 500,000 g/mol. These may consist of linear and thus unbranched chains. All sugar compounds known to the skilled person and appearing suitable are considered as sugars of this type. Thus, for example, celluloses and starches can be mentioned, whereby one or at least two different starches are examples. Among starches, in turn amylase-containing starches are preferred. The amylase content may lie within a range from about 10 wt % to about 80 wt %, or within a range from about 20 wt % to about 70 wt %, based upon the starches. The di- or polysugars may have a particle size such that at least about 50 wt %, or at least about 70 wt %, or at least about 85 wt % of the particles are smaller than 50 µm. The particle size is determined by means of sieve analysis. Such products are, for example, commercially available under the trade name Eurylon 7 or Foralys 380 from the company Roquette, Lestrem, France.

Such water-absorbing polymer structures may be prepared and may thus obtainable by
  providing a surface crosslinked water-absorbing polymer; and
  mixing the surface crosslinked water-absorbing polymer with a di- or polysugar.

The water-absorbing polymer may be based to at least about 50 wt %, or at least about 80 wt %, or at least about 95 wt % upon acrylic acid which comes from the inventive dehydration process used for polymerization partially neutralized, and with a crosslinker.

The sustainability factor gives the proportion of the polymer structure which is based upon materials based upon non-fossil, renewable organic materials. A sustainability factor of 100 means that the polymer structure is fully based upon non-fossil, renewable organic material.

A further contribution to the solution of the above-described objects is provided by a composite comprising the water-absorbing polymer structures according to the invention or water-absorbing polymer structures that are obtainable by radical polymerization of the acrylic acid obtainable by the above-described synthetic process in the presence of cross-linkers. It is preferred that the polymer structures according to the invention and the substrate are firmly bound together. As substrates, sheets made from polymers, such as, for example, made from polyethylene, polypropylene or polyamide, metals, non-woven material, fluff, tissues, woven materials, natural or synthetic fibers, or other foams are preferred. It is, furthermore, preferred according to the invention that the polymer structures may be comprised in the composite in an amount of at least about 50 wt %, or at least about 70 wt %, or at least about 90 wt %, based upon the total weight of polymer structure and substrate.

In another embodiment of the composite according to the invention, the composite may be a sheet-like composite, as described in WO-A-02/056812 as "absorbent material". The disclosure of WO-A-02/056812, in particular and limited with respect to the exact construction of the composite, the mass per unit area of its components as well as its thickness is hereby introduced as reference.

A further contribution to the solution of the above-mentioned objects is provided by a process for producing a composite, whereby the water-absorbing polymer structures according to the invention, or the water-absorbing polymers, which may be obtained by radical polymerization of the acrylic acid obtainable by the above-described synthetic process in the presence of cross-linkers, and a substrate and optionally an additive are brought into contact with each other. Substrate may include those substrates that have already been mentioned in connection with the composite according to the invention.

A contribution to the solution of the above-mentioned objects is also provided by a composite obtainable by the above-described process.

A further contribution to the solution of the above-mentioned objects is delivered by chemical products comprising the water-absorbing polymer structures according to the invention or a composite according to the invention. Preferred chemical products are in particular foams, moulded bodies, fibers, sheets, films, cables, sealing materials, liquid-absorbing hygiene articles, in particular diapers and sanitary napkins, carriers for plant or fungus growth-regulating agents or plant protection agents, additives for construction materials, packaging materials, or soil additives.

The use of the water-absorbing polymer structure according to the invention or of the composite according to the invention in chemical products, preferably in the above-mentioned chemical products, in particular in hygiene articles such as diapers or sanitary napkins, as well as the use of the superabsorbent particles as carriers for plant- or fungus-growth-regulating agents or plant protection active substances make a contribution to the solution of the above-mentioned objects. In the use as carrier for plant- or fungus-growth-regulating agents or plant protection active substances, it is preferred that the plant- or fungus-growth-regulating agents or plant protection active substances may be released over a period of time controlled by the carrier.

A particular contribution to the solution of the above-mentioned objects may also be made by the use of acrylic acid obtained by a synthesis process, which comprises the following process step:

splitting of an organic material by means of enzymes or at least one enzyme component, in the production of water-absorbing polymer structures.

A contribution to the solution of the above-mentioned objects is also made by a device for production of acrylic acid comprising the following device components connected with each other in fluid-conveying manner:

(γ1_1) at least one bioreactor comprising
(γ1_1) a reaction space,
(γ1_2) a feed line for an organic material,
(γ1_3) a feed line for nutrients or nutrient solutions,
(γ1_4) an exit line for a β-hydroxypropionic acid-comprising reaction mixture,
(γ1_5) at least one stirring device,
(γ1_6) at least one heating device,
(γ1_7) optionally, at least one aeration unit, and
(γ1_8) optionally, at least one measuring probe;
(γ2) a first purification unit for purification of β-hydroxypropionic acid, connected in fluid-conveying manner to the exit line (γ1_4) of the bioreactor (γ1);
(γ3) a dehydration reactor connected to the purification unit (γ2), comprising
(γ3_1) a reaction space, comprising a catalyst,
(γ3_2) a feed line for purified β-hydroxypropionic acid,
(γ3_3) an exit line for an acrylic acid-comprising reaction mixture, and
(γ3_4) at least one heating device,
(γ4) optionally, a second purification unit for purification of acrylic acid, connected with the exit line (γ3_3).

By "fluid-conveying" is understood according to the invention that gases or liquids, including suspensions, or their mixtures are conducted through appropriate lines. In particular, pipes, pumps, and the like can be used.

As bioreactors (γ1), all types of reactors known to the skilled person may be used, in which organic material may be broken down under the effect of microorganisms. In so far as a fermentation process with participation of microorganisms in the splitting of organic materials is carried out in the reactor, it is preferred that the reactor, in addition to a suitable stirring device, also comprises measuring probes, preferably for determination of the pH value, of the $CO_2$ concentration, and of the temperature. Furthermore, the bioreactor may also comprise a carrier material, upon the surface of which the microorganisms are immobilized. Carrier materials for the immobilization of microorganisms may include porous stones, for example lava or expanded clay, as well as coals and different types of bodies made from artificial materials.

The particle size varies depending on the type of material and the size of the bioreactor, preferably between about 5 mm and about 50 mm.

Reactors that comprise a carrier material, upon the surface of which enzymes that enable the splitting of an organic material to form β-hydroxypropionic acid are immobilized can, however, also be used as bioreactors.

The first purification unit for β-hydroxypropionic acid (γ2) can, for example, be a multi-step separating system provided with an ultrafilter as pre-filter, as described in DE-A-197 18 608. The dehydration reactor (γ3) is preferably a pipe bundle reactor with or without catalyst fill, or a ripple bed reactor.

The second purification unit (γ4) may be any purification unit known to the skilled person, which is used for purification of acrylic acid obtained by gas phase oxidation of propylene. These purification units preferably comprise distillation devices and/or crystallization devices.

A contribution to the solution of the above-mentioned objects is also made by a process for production of acrylic acid from carbohydrates, wherein the above-described device is used. The acrylic acid obtainable by this process also makes a contribution to the solution of the above-mentioned objects. This acrylic acid is preferably characterized by at least one, preferably all of the following properties:

an aldehyde content, in particular benzaldehyde, of less than about 5 ppm, or less than about 1 ppm, or less than about 0.1 ppm, or less than about 0.01 ppm;

a maleic acid or maleic acid anhydride content of less than about 5 ppm, or less than about 1 ppm, or less than about 0.1 ppm, or less than about 0.01 ppm;

an acetic acid content of less than about 5 ppm, or less than about 1 ppm, or less than about 0.1 ppm, or less than about 0.01 ppm; and a ketone content, in particular PTA, of less than about 5 ppm, or less than about 1 ppm, or less than about 0.1 ppm, or less than about 0.01 ppm.

The invention is now more closely described by means of non-limiting figures and examples.

FIG. 1 shows a device according to the invention for production of acrylic acid, in which a dehydration occurs in the gas phase.

Figure 2:
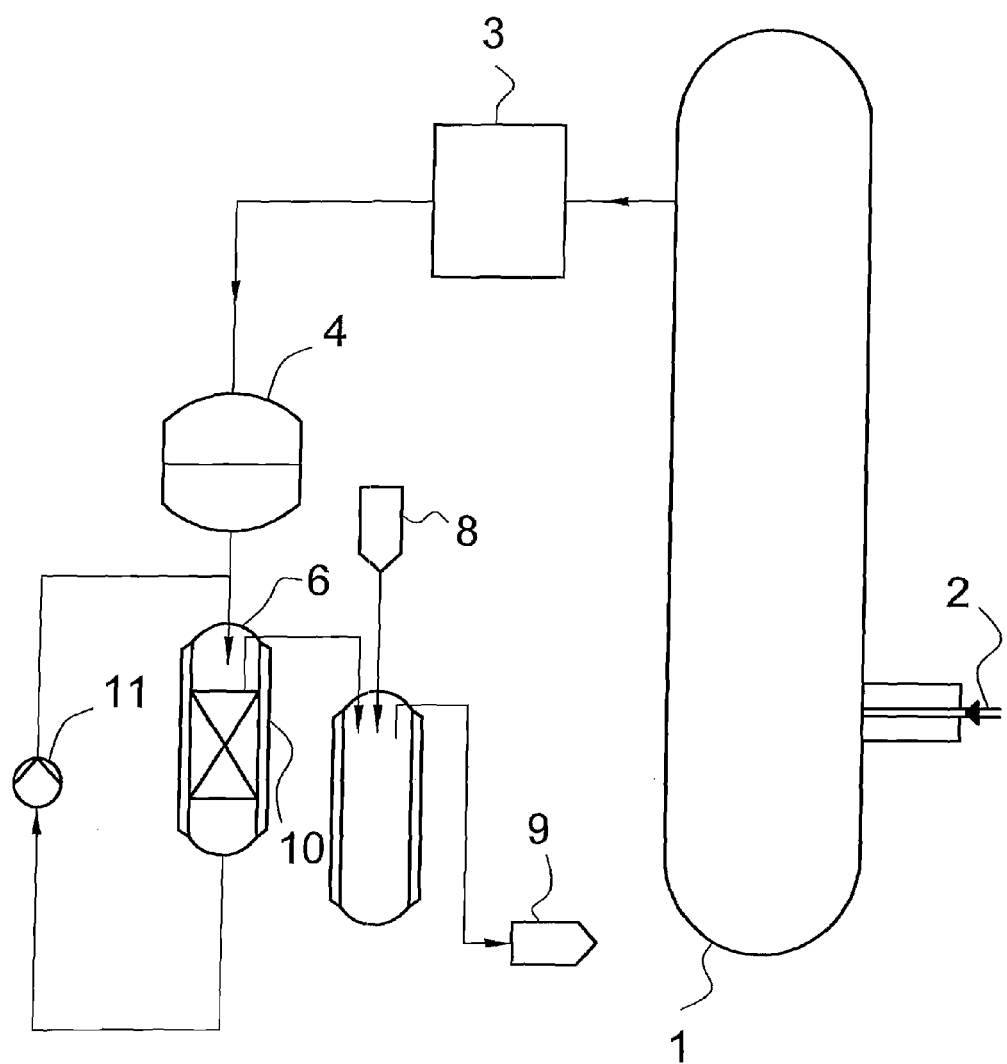
FIG. 2 shows a device according to the invention for production of acrylic acid, in which a dehydration occurs in the liquid phase.

FIG. 2 shows a device according to the invention for production of acrylic acid, in which a dehydration occurs in the liquid phase.

According to FIG. 1, the organic material to be split, which is preferably carbohydrates, particularly preferably glucose, is introduced via feed line 2 into a bioreactor 1, in which a suitable nutrient medium is situated. Furthermore, microorganisms can be present in the bioreactor suspended in the nutrient medium or immobilized on a substrate. It is also conceivable that enzymes which catalyze the splitting of the organic material into β-hydroxypropionic acid are immobilized on a suitable substrate. After the splitting of the organic material, the fermentation broth is purified in a first purification device 3. This purification device 3 preferably comprises an ultrafilter with an opening size within a range from 20 kDa to 200 kDa as pre-filter for the separation of the cells as well as further device components such as, for example, electrodialysis devices, with which a purification of the β-hydroxypropionic acid occurs. The purified β-hydroxypropionic acid is transferred either in pure form or in the form of an aqueous solution into a container 4 as compound receiver. From here, the β-hydroxypropionic acid or the aqueous solution comprising the β-hydroxypropionic acid respectively passes into an evaporator 5, which comprises a heating device 10, in which the individual components of the composition are evaporated. The thus-obtained gas phase is then brought into contact with a catalyst bed 6, which is preferably based upon a porous material impregnated with phosphoric acid and can likewise be heated to the desired dehydration temperature by means of a heating device 10. The gaseous composition comprising water and acrylic acid obtained after passing the catalyst bed is condensed in a condensation device 7 to obtain an aqueous acrylic acid solution. Optionally, additional solvent, such as water, can be added via a feed line 8, for absorption of the acrylic acid. Via a feed line 9, the aqueous acrylic acid solution can be conducted to further purification devices, in particular crystallization and/or distillation devices, in order to obtain an acrylic acid which is as pure as possible.

The production of acrylic acid in which a liquid phase dehydration occurs (FIG. 2) occurs substantially in the same way as the gas phase dehydration depicted in FIG. 1. However, the β-hydroxypropionic acid or the aqueous solution comprising the β-hydroxypropionic acid respectively obtained after the purification of the fermentation solution is not evaporated by means of an evaporator, but rather transferred in liquid form to the reactor for dehydration. In order to achieve as full a dehydration as possible, it can be advantageous to conduct the aqueous β-hydroxypropionic acid solution by means of a pump 11 in the cycle, as shown in FIG. 2.

EXAMPLES

The following examples and preproducts for the examples are provided to illustrate the invention and do not limit the scope of the claims. Unless otherwise stated, all parts and percentages are by weight.

Example 1

Preparation of Post-Crosslinked Polymer

β-hydroxypropionic acid was produced by a fermentation route according to example 8 of WO-A-02/42418. From the fermentation solution freed from cells, the β-hydroxypropionic acid was separated from the composition according to example 2 of WO-A-02/090312. The pure β-hydroxypropionic acid obtained in this way was converted to acrylic acid in a gas phase dehydration. As catalyst, 100 g Rosenthal balls ($\alpha$-$Al_2O_3$) with a diameter of 3 mm are used, which have been previously mixed with 25 g of a 20 wt. % phosphoric acid solution for one hour. The excess water is removed using a rotary evaporator at 80° C. 100 ml of this catalyst ($-5.6 > H_0 > -3$) are placed in a steel pipe with diameter 15 mm.

The aqueous acrylic acid solution obtained after the dehydration of the β-hydroxypropionic acid is purified by azeotropic distillation according to the teaching of DE-A-198 53 064. The acrylic acid obtained in this way contained no measurable amounts of PTA or benzaldehyde.

Dissolved oxygen was removed from a monomer solution consisting of 280 g of the above-obtained acrylic acid, which was neutralized to 70 mol. % with sodium hydroxide, 466.8 g water, 1.4 g polyethylene glycol-300-diacrylate, and 1.68 g allyloxypolyethyleneglycol acrylic acid ester by flushing with nitrogen and the monomer solution cooled to the start temperature of 4° C. After reaching the start temperature, the initiator solution (0.1 g 2,2'-azobis-2-amidinpropane dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) was added. After the end temperature of approximately 100° C. was reached, the gel formed was comminuted and dried for 90 minutes at 150° C. The dried polymer was coarsely chopped, ground, and sieved to a powder with a particle size of 150 to 850 µm.

For post-crosslinking, 100 g of the above-obtained powder was combined with a solution of 1 g 1,3-dioxalan-2-one, 3 g water, and 0.5 g aluminium sulphate-18-hydrate and then heated for 40 minutes in an oven set to 180° C.

Example 2

Preparation of a Biodegradable Polymer

The post-crosslinked polymer obtained in Example 1 was mixed under dry conditions with a water-soluble wheat starch (the product Foralys® 380 from the company Roquette, Lestrem, France) in the weight ratio polymer:starch of 4:1 and then homogenized for 45 minutes on an overhead shaker, type BTR 10 from the company Frobel GmbH, Germany.

The product had a biodegradability according to the modified Sturm test after 28 days of 40% and a CRC value of 30 g/g. The sustainability factor was about 99.

LIST OF REFERENCE NUMBERS 1 bioreactor
2 feed line for organic material to be split
3 first purification device
4 compound receiver
5 evaporator
6 catalyst bed of the dehydration reactor
7 condensation device
8 feed line for a solvent
9 product outlet for further processing of the acrylic acid
10 heating element
11 pump Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

What is claimed is:

1. A process of producing a polymer by radical polymerization of acrylic acid, comprising the steps of:
   A) forming β-hydroxypropionic acid by splitting an organic material comprising a carbohydrate in the presence of a microorganism and a nutrient solution comprising carbon sources, nitrogen sources, and salts thereof for the nutrition of the microorganism, by means of an enzyme or at least one component of an enzyme;
   B) purifying the product of step A) including the step of removing the β-hydroxypropionic acid from the nutrient solution to provide β-hydroxypropionic acid;
   C) dehydrating the β-hydroxypropionic acid of step B) to form an aqueous acrylic acid solution;
   D) purifying the aqueous acrylic acid solution of step C) by crystallization to have a benzaldehyde content of less 0.1 ppm, a maleic acid or maleic acid anhydride content of less than about 5 ppm, an acetic acid content of less than 0.1 ppm and a ketone content of less than about 5 ppm, wherein the purification includes removal of water from the aqueous acrylic acid solution to form acrylic acid; and
   E) polymerizing the acrylic acid of step D) by radical polymerization to produce the polymer.

2. The process according to claim 1, wherein step E) comprises the steps of:
   i) polymerizing the acrylic acid of step D) by radical polymerization in the presence of a crosslinker to form a polymer gel;
   ii) comminuting the polymer gel;
   iii) drying the polymer gel to obtain water-absorbing polymer structures; and
   iv) surface post-treating the water-absorbing polymer structure.

3. The process according to claim 2, wherein step C) comprises catalytic dehydration of the β-hydroxypropionic acid.

4. The process according to claim 3, wherein the dehydration of the β-hydroxypropionic acid occurs in the liquid phase or in the gas phase.

5. The process according to claim 3, wherein a porous carrier brought into contact with an inorganic acid is used as a catalyst.

6. The process according to claim 5, wherein at least about 90 wt % of the porous carrier is a silicon oxide.

7. The process according to claim 5, wherein the inorganic acid is phosphoric acid.

8. The process according to claim 5, wherein the porous carrier has a surface area within a range from about 0.005 m$^2$/g to about 450 m$^2$/g.

9. The process according to claim 2, wherein at least about 75 wt % of the organic material is a carbohydrate.

10. The process according to claim 2, wherein at least about 80% of the acrylic acid is obtained by a synthetic process comprising the step of splitting an organic material by means of an enzyme or at least one component of an enzyme.

* * * * *

UNITED STATES PATENT AND TRADEMARK OFFICE
CERTIFICATE OF CORRECTION

PATENT NO. : 8,703,450 B2
APPLICATION NO. : 11/817204
DATED : April 22, 2014
INVENTOR(S) : Günther Bub et al.

It is certified that error appears in the above-identified patent and that said Letters Patent is hereby corrected as shown below:

In the Specification

Column 9,

Line 14, "thereof Such" should read -- "thereof. Such --.

Line 23, "from Sildchemie AG" should read -- from Südchemie AG --.

Column 14,

Lines 60-61, "name Eurylon 7 or Foralys 380 from" should read -- name Eurylon® 7 or Foralys® 380 from --.

Column 19,

Line 3, "company Frobel GmbH" should read -- company Fröbel GmbH --.

Signed and Sealed this
Twenty-fourth Day of June, 2014

Michelle K. Lee
*Deputy Director of the United States Patent and Trademark Office*